United States Patent
Axelsson et al.

(10) Patent No.: US 7,459,144 B2
(45) Date of Patent: Dec. 2, 2008

(54) PROCESS FOR PREPARATION OF MR CONTRAST AGENTS

(75) Inventors: Oskar Axelsson, Malmo (SE); Charlotte Olofsson, Malmo (SE); Axel Morgenstjerne, Lyngby (DK); Georg Hansson, Malmo (SE); Haukur Johannesson, Malmo (SE); Jan-Henrik Ardenkjaer-Larsen, Malmo (SE)

(73) Assignee: GE Healthcare AS, Oslo (NO)

( * ) Notice: Subject to any disclaimer, the term of this patent is extended or adjusted under 35 U.S.C. 154(b) by 719 days.

(21) Appl. No.: 11/002,864

(22) Filed: Dec. 2, 2004

(65) Prior Publication Data

US 2005/0152840 A1    Jul. 14, 2005

Related U.S. Application Data

(60) Division of application No. 09/990,537, filed on Nov. 16, 2001, now Pat. No. 6,872,380, which is a continuation of application No. PCT/GB00/01897, filed on May 17, 2000.

(60) Provisional application No. 60/139,259, filed on Jun. 15, 1999.

(30) Foreign Application Priority Data

May 19, 1999 (GB) .................. 9911681.6

(51) Int. Cl.
 *A61B 5/055* (2006.01)
 *B01J 10/00* (2006.01)
(52) U.S. Cl. ........................ 424/9.3; 422/189
(58) Field of Classification Search ............. 422/189
See application file for complete search history.

(56) References Cited

U.S. PATENT DOCUMENTS 4,194,051 A   3/1980  Bachman et al.
(Continued)

FOREIGN PATENT DOCUMENTS

WO         93/30918         7/1998
(Continued)

OTHER PUBLICATIONS

U.S. Appl. No. 60/066,570, filed Mar. 1998, Golman, et.al.
(Continued)

*Primary Examiner*—Glenn Caldarola
*Assistant Examiner*—Natasha Young
(74) *Attorney, Agent, or Firm*—Robert F. Chisholm

(57) ABSTRACT

The present invention provides a process for the preparation of an MR contrast agent, said process comprising:
 i) obtaining a solution in a solvent of a hydrogenatable, unsaturated substrate compound and a catalyst for the hydrogenation of said substrate compound;
 ii) introducing said solution in droplet form into a chamber containing hydrogen gas ($H_2$) enriched in para-hydrogen (p-$^1H_2$) and/or ortho-deuterium (o-$^2H_2$) whereby to hydrogenate said substrate to form a hydrogenated imaging agent;
 iii) optionally subjecting said hydrogenated imaging agent to a magnetic field having a field strength below earth's ambient field strength;
 iv) optionally dissolving said imaging agent in an aqueous medium;
 v) optionally separating said catalyst from the solution of said imaging agent in said aqueous medium;
 vi) optionally separating said solvent from the solution of said imaging agent in said aqueous medium; and
 vii) optionally freezing the solution of said imaging agent in said aqueous medium.

5 Claims, 4 Drawing Sheets

U.S. PATENT DOCUMENTS 5,618,970 A * 4/1997 Challenger .................. 560/121
6,574,495 B1 6/2003 Golman et al.

FOREIGN PATENT DOCUMENTS

WO 99/24080 5/1999
WO 00/40988 7/2000

OTHER PUBLICATIONS

U.S. Appl. No. 60/076,924, filed Nov. 1997, Golman, et.al.

A. Harthun, et.al. "The Use of In Situ NMR Spectroscopy and Parahydrogen as Tools for Chiral Synthesis" Tetrahedron Letters, NL, Elsevier Science Publishers, Amsterdam vol. 36, No. 41, Oct. 9, 1995, pp. 7423-7426.

J. Barkemeyer, et.al. "Hetero-NMR Enhancement Via Parahydrogen" Journal of the American Chemical Society, U.S., American Chemical Society, Washington, D.C. vol. 117, 1995 pp. 2927-2928.

J. Natterer, et.al. "Parahydrogen Induced Polarization" Progress in Nuclear Magnetic Resonance Spectroscopy, GB, Pergamon Press, Oxford vol. 31, No. 4, Nov. 1997, pp. 293-315.

J. Brown, et.al. "Stereoselective Homogeneous Hydrogenation of 3-Substitued Itaconate Esters" J. Chem. Soc., Chem. Commun. 1987, No. 3, pp. 181-182.

* cited by examiner

PROCESS FOR PREPARATION OF MR CONTRAST AGENTS

This application is a division of U.S. application Ser. No. 09/990,537 filed Nov. 16, 2001 now U.S. Pat. No. 6,872,380 which is a continuation of international application number PCT/GB00/01897 filed May 17, 2000 which claims priority to application number 9911681.6 filed May 19, 1999 in Great Britain and to U.S. provisional application No. 60/139,259 filed Jun. 15, 1999, the entire disclosure of which is hereby incorporated by reference.

FIELD OF THE INVENTION

Backround of Invention

Hydrogen molecules ($^1H_2$) exist in two different forms, namely para-hydrogen where the nuclear spins are anti-parallel and out-of-phase (the singlet state) and ortho-hydrogen where they are parallel or anti-parallel and in-phase (the triplet state). At room temperature, the two forms are in equilibrium with an approximately 1:3 ratio of para to ortho hydrogen. At 80K the ratio is about 48:52 and at 20K it approaches 100:0 (actually about 99.8:0.2).

In contrast, deuterium ($D_2$ or $^2H_2$), where the $^2H$ nucleus has a nuclear spin (S) of 1 rather than ½, exists in nine different forms, three anti-symmetric para forms and six symmetric ortho forms. At ambient temperature, the ratio of ortho-deuterium (o-$D_2$) to para-deuterium (p-$D_2$) in an ortho-/para-deuterium mixture is about 2:1, at 60K it is about 3:1 and at 20K it is about 98:2. (Deuterium freezes at about 19K).

In WO99/24080, which is hereby incorporated by reference, it is described how para-hydrogen may be used to catalytically hydrogenate unsaturated compounds, transferring to those compounds the anti-parallel proton spins of the para-hydrogen molecule, and transferring nuclear spin polarization from the para-hydrogen deriving protons to non-hydrogen non-zero nuclear spin (i.e. S≠0) nuclei in the hydrogenated compound, e.g. $^{13}C$ or $^{15}N$ nuclei. In this way, such non-zero spin nuclei may be given a nuclear spin polarization (hyperpolarization) equivalent to that achieved in a kiloTesla or higher magnetic field. The nuclear magnetic resonance signal emitted by such hyperpolarized nuclei may be used for magnetic resonance imaging in much the same way as has been done with hyperpolarized $^3He$-MRI.

While WO99/24080 does describe means by which para-hydrogen hydrogenation may be effected, we have now found that hydrogenation to harness for MIRI the p-$H_2$ and!or o-$D_2$ induced hyperpolarization, the hydrogenation reaction is particularly favourably performed by mixing gaseous para-hydrogen and/or ortho-deuterium enriched hydrogen (i.e. where the p:o ratio of $^1H_2$ is greater than 1:3, particularly greater than 3:7, more particularly greater than 1:1 and/or the o:p ratio of $^2H_2$ is greater than 3:2, particularly greater than 3:1, more particularly greater than 4:1) with a spray of a solution of the unsaturated compound and a hydrogenation catalyst.

SUMMARY OF INVENTION

In view of the needs of the prior art, the present invention provides a hydrogenation apparatus including a hydrogenation chamber having a liquid outlet, a conduit, a liquid droplet generator inlet, and a solvent removal chamber. The liquid outlet opens into the conduit. The conduit leads to the liquid droplet generator inlet which then leads into the solvent removal chamber. The hydrogenation chamber includes a hydrogen inlet and a solution inlet provided with a further liquid droplet generator. The conduit includes a catalyst removal chamber between the hydrogenation chamber and the solvent removal chamber and is provided with a liquid inlet. The solvent removal chamber is provided with a gas outlet and with a liquid outlet.

A similar nuclear spin hyperpolarization may likewise be achieved by hydrogenation with deuterium, more particularly with o-deuterium or with hydrogen ($^1H_2$)/deuterium($^2H_2$) mixtures, particularly deuterium or hydrogen/deuterium mixtures in which the p/o ratio for hydrogen and the o/p ratio for deuterium are higher than the equilibrium values (1:3 and 2:1) at ambient temperature, e.g. having ratios corresponding to the equilibrium values at temperatures below 80K, more particularly temperatures below 40K, especially between liquid helium (4K) temperatures and 30K, more especially at temperatures between the melting points of the hydrogen and/or deuterium and 25K.

The hydrogenation and/or deuteration, e.g. of an unsaturated bond in a substrate molecule whereby to introduce a $^1H$ or $^2H$ atom bound to each of the atoms linked by the unsaturated bond, serves to introduce a hydrogen/deuterium spin distribution into the hydrogenated substrate molecule which is other than the equilibrium distribution at ambient temperature. Where the substrate molecule contains non-zero nuclear spin nuclei (in natural or above natural isotopic abundances), particularly where these non-zero spin (S≠0) nuclei are close in the molecular structure of the hydrogenated substrate to the $^1H$ or $^2H$ atoms introduced by the hydrogenation, the introduction $^1H$ or $^2H$ atoms can induce a nuclear spin distribution in the S≠0 nuclei which is other than the equilibrium distribution at ambient temperature. These non-equilibrium nuclear spin distributions for the introduced protons/deuterons and for the S≠0 nuclei in the hydrogenated substrate may be harnessed to provide signal enhancement in magnetic resonance imaging (MRI) techniques, including in vivo MRI.

The term "hyperpolarization" is used herein to denote a nuclear spin population distribution for a non-zero nuclear spin imaging nucleus in a hydrogenated substrate which is other than the equilibrium population distribution at ambient to physiological (e.g. 25-40° C.) temperatures, more particularly for non-zero nuclear spin imaging nuclei in a hydrogenated substrate a distribution in which the population difference between ground and excited nuclear spin states is greater than the equilibrium population difference.

By "imaging nuclei" is meant the nuclei in the hydrogenated substrate responsible for the MR signal used in MRI to generate images. Thus, for example, the imaging nucleus might be a $^{13}C$ or $^{15}N$ nucleus, generally up to 4 bonds away from a $^1H$ or $^2H$ nucleus introduced by hydrogenation of the substrate, or it may be a $^1H$ or a $^2H$ nucleus introduced by hydrogenation of a non-symmetric unsaturated substrate. (Since the substrate is unsymmetrical the resonance frequencies of the two introduced hydrogens will not be the same).

DETAILED DESCRIPTION OF THE INVENTION

Figure 1:
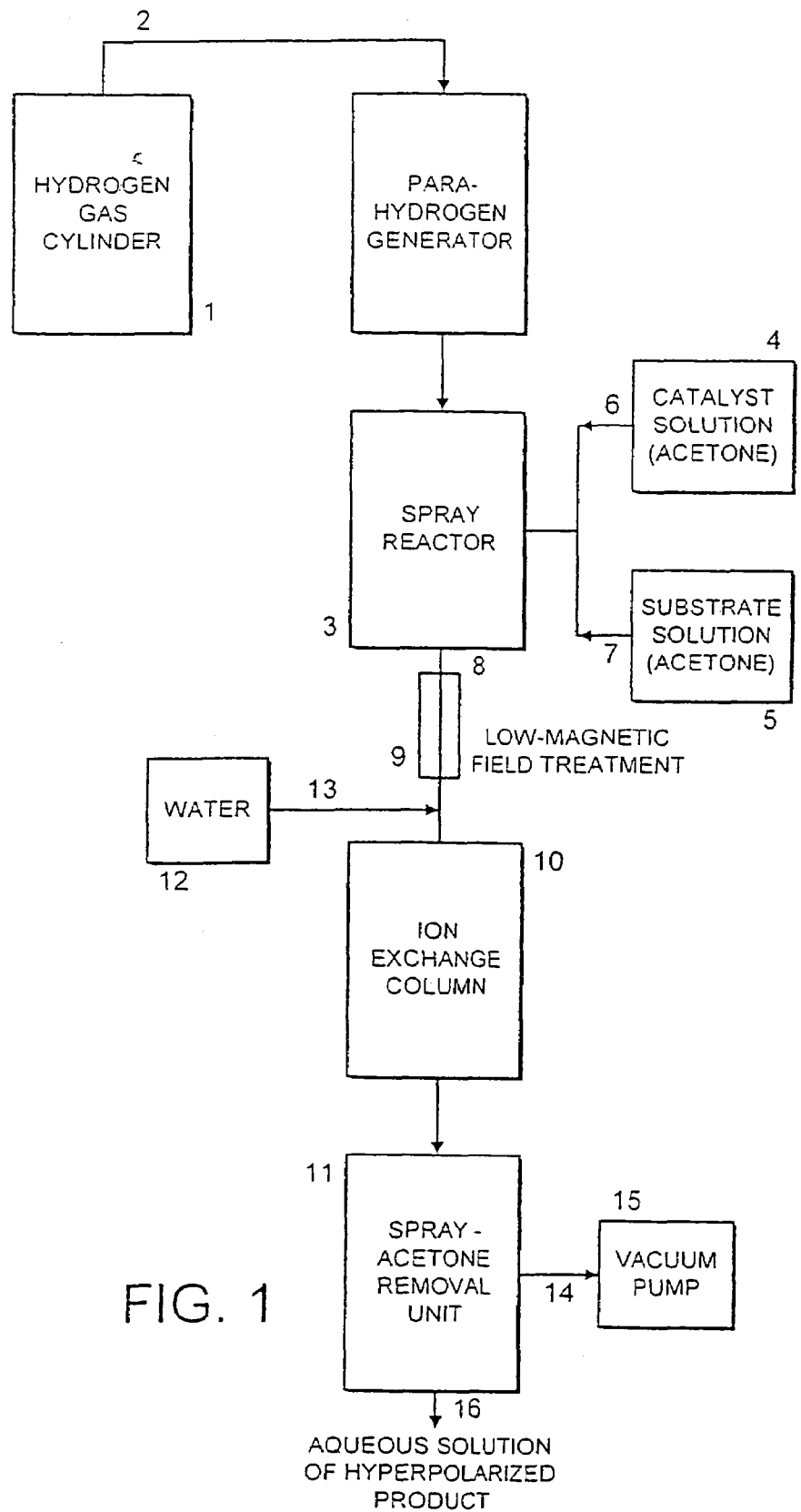
FIG. 1 is a schematic view of one apparatus according to the invention.

Viewed from one aspect the invention thus provides a process for the preparation of an MR contrast agent, said process comprising:

i) obtaining a solution in a solvent of a hydrogenatable, unsaturated substrate compound and a catalyst for the hydrogenation of said substrate compound;

ii) introducing said solution in droplet form into a chamber containing hydrogen gas ($H_2$) enriched in para-hydrogen (p-$^1H_2$) and/or ortho-deuterium (o-$^2H_2$) whereby to hydrogenate said substrate to form a hydrogenated imaging agent;

iii) optionally subjecting said hydrogenated imaging agent to a magnetic field having a field strength below earth's ambient field strength;

iv) optionally dissolving said imaging agent in an aqueous medium;

v) optionally separating said catalyst from the solution of said imaging agent in said aqueous medium;

vi) optionally separating said solvent from the solution of said imaging agent in said aqueous medium; and vii) optionally freezing the solution of said imaging agent in said aqueous medium.

In optional step (iii) of the process of the invention, the hydrogenated imaging agent is subjected to a low magnetic field treatment—this step is desirably effected unless the MR imaging procedure is to use as imaging nuclei deuterons introduced by deuteration with ortho-$D_2$ (i.e. gas comprising $D_2$ where the o-$D_2$:p-$D_2$ ratio is greater than 2:1). The low field treatment may be effected at any stage following onset of hydrogenation, and indeed the process of the invention may be performed in its entirety in a low field; however it is desirable that the low field treatment occur before water addition (optional step (iv)) in order both to avoid enhancement by the low field of hyperpolarization loss induced by paramagnetic materials which may be present (e.g. as minor impurities, or as dissolved oxygen) in the water and because protons in the water would themselves have a relaxing effect. Accordingly it is preferred that the low field treatment be of the hydrogenation reaction medium (e.g. by placing at least part of the chamber in a low field) and/or of the reaction medium drawn out from the chamber. Low field treatment (e.g. at fields below 50µT, preferably less than 1 µT, most preferably less than 0.1 T) may be achieved by magnetic shielding using commercially available materials, e.g. µ-metal, and may be particularly suitably achieved by disposing some or all of the apparatus used for the process of the invention in a magnetically shielded container such as is described in WO99/17304.

The low magnetic field treatment may alternatively be effected by passage through a twin µ-metal layer tube, capable of giving a field of less than 1 µT, more preferably less than 0.5 µT, most preferably less than 0.1 µT, inside.

Preferably, the low field treatment may be effected by passage through a magnetically shielded area with a special magnetic field profile. The magnetic screen is a multi-layer tube of µ-metal with the layers arranged so that the sample leaves the earth's magnetic field and enters an area with a field lower than 0.1 µT in just a few ms. The sample is then gradually returned to the earth's magnetic field by a combination of a spiral-shaped tube and a lower degree of magnetic shielding. This effects an efficient transfer of polarization from protons to the hetero-nucleus.

This cycling of the external magnetic field from "earth-field" to less than 1 µT, preferably about 0.1 µT, and then gradually back again enables polarisation to be transferred from protons in the freshly hydrogenated contrast agent to a nucleus within the same molecule with a longer polarisation life-time, preferably a $^{13}C$ or $^{15}N$ atom. The timing of this process is critical. For the process to work as effectively as possible the sample should leave the earth-field suddenly and then gradually return to earth field. In the present context, "suddenly" means of the order of 1 ms and "gradually" means of the order of 10-10000 ms, preferably 100-1000 ms.

The magnetic-field screen can be made from µ-metal and can consist of three concentric tubes, for example with diameters of 80, 25 and 12 mm, respectively. At one end of the screen all three layers overlap to give maximal screening and the glass tube is straight and with an inner diameter of, for example 1 mm. From the middle of the screen only the outer layer of screening is kept and the tube spirals out and the inner diameter is increased to, for example 3 mm, to give a more gradual increase in the field. The spiral continues past the screen for a few centimeters.

The magnetic screen is also equipped with demagnetization coils since the µ-metal is slowly magnetized by external fields, especially in the vicinity of imaging magnets. The demagnetization process involves running AC current of approximately 5 A and 50 Hz through the demagnetization coils and then gradually decreasing the current to zero. The whole process should take between one and a few minutes and preferably be performed on a daily basis. The coils can be made from 1 mm varnished copper wire and can have in total approximately 2000 turns.

A stopped flow system is where the newly-produced para-hydrogenated product is passed into a resistive magnet (coil) inside a magnetically shielded region. The magnetic screen may be a two-layer tube of µ-metal with such screening capacity that the residual field is less than 0.1 µT when no current is flowing in the coil. Initially, when the sample enters the coil, the current is on to produce a magnetic field of the order of the earth's field. The current is then turned off and then gradually increased back to the original. This effects an efficient transfer of polarization from protons to the hetero-nucleus.

Most imaging agents will require this low magnetic field treatment for one of two reasons, first that this promotes polarization transfer from the introduced $^1H$ or $^2H$ nuclei to the imaging nuclei (e.g. $^{13}C$, $^{15}N$, etc.) and secondly as the treatment transforms the line shape of the MR signal from an anti-phase multiplet with zero integral to a multiplet with a net signal which is good for imaging.

The hydrogenatable substrate used may be a material such as is discussed in WO99/24080 as a para-hydrogenation substrate. For in vivo imaging studies, the substrate is preferably a material which is physiologically tolerable both in hydrogenated and unhydrogenated forms. For $^2$D-MR studies, the substrate is desirably non-symmetrical about the unsaturated bond which is hydrogenated, especially preferably non-symmetrical within 4 bonds of the unsaturated bond (e.g. $H_5C_2OOCCH_2CH=CH-CH_3$ would be considered to be unsymmetrical within 2 bonds of the ethylenic C:C double bond).

For in vitro or in vivo MR studies of biological or quasi-biological processes or synthetic polymer (e.g. peptide, polynucleic acid etc.) syntheses, the substrate is preferably hydrogenatable to form a molecule participating in such reactions, e.g. an amino acid, a nucleic acid, a receptor-binding molecule, etc., either a natural such molecule or an analog.

The solvent used in step (i) of the process of the invention may be any convenient material which serves as a solvent for the substrate and the hydrogenation catalyst. Preferably however it is a volatile organic solvent (e.g. acetone) especially one which is water miscible, especially preferably it is not water (i.e. not $^1H_2O$) and especially preferably it is perdeuterated (e.g. $C^2H_3OC^2H_3$ or $d_6$-acetone). Where the imaging agent is for use in in vivo MR investigations, the solvent is preferably physiologically tolerable. Solvent removal (optional process step (vi)) is preferably effected by vacuum, e.g. by spray-flash distillation. Other rapid solvent removal techniques, e.g. affinity techniques, may however be used.

The solvent is preferably used at or near the minimum quantities required to maintain substrate, catalyst and imaging agent in solution during the hydrogenation reaction.

Alternatively, the reaction may be performed directly in water using a water-soluble substrate and a water-soluble catalyst. The process in this case is both simpler and faster as the step of solvent removal is not then required.

The hydrogenation catalyst is preferably a catalyst as discussed in WO99/24080, e.g. a metal complex, in particular a rhodium complex.

The enriched hydrogen, which may be pure $^1H_2$ or $^2H_2$, or a mixture of $^1H_2$ and $^2H_2$ (perhaps containing some HD), optionally containing other gases although preferably free from oxygen or other reactive or paramagnetic gases, may be prepared by cooling hydrogen (i.e. $^1H_2$, $^2H_2$ etc.), preferably to a temperature below 80K, more preferably to a temperature below 30K, still more preferably to a temperature below 22K, and allowing the nuclear spin states to equilibrate, optionally in the presence of a solid phase equilibration promoter, e.g. $Fe_3O_4$, $Fe_2O_3$, activated charcoal, etc. The enriched hydrogen is then preferably removed from the equilibrator and optionally stored before use, preferably at a reduced temperature, e.g. 20-80K. The preparation and storage of enriched hydrogen is described in WO99/24080 the contents of which are incorporated herein by reference.

For the hydrogenation reaction, enriched hydrogen is filled into a reaction chamber optionally under pressure, e.g. 50 to 100 bar, and the catalyst and substrate solution is introduced in droplet form, e.g. by spraying or atomizing, into this reactor. If desired, the solution may be produced by mixing separate solutions of catalyst and of substrate. To ensure proper mixing, a distributor or a plurality of spray nozzles may be used and the chamber contents may be mixed, e.g. by a mechanical stirrer or by appropriately shaping the chamber walls where there is a flow of reaction mixture in the chamber. The spray nozzles are advantageously of the pneumatic-type where para-hydrogen is used as the atomising gas. Such nozzles give a better mixing of gas and liquid, smaller droplets and faster spraying than hydrostatic spray nozzles. The process may be performed continuously with a flow reactor, e.g. a loop or tube reactor, or alternatively it may be a batch-wise process. Preferably however there will be a continuous or pulsed flow of enriched hydrogen and solution-spray into the reactor, a continuous or batch-wise removal of liquid solution from the base of the reactor, and a continuous or batch-wise venting of unreacted gas from the reactor. The enriched hydrogen and solution passing into the reactor are preferably temperature-controlled to ensure the gas-droplet phase in the reactor is at the desired temperature. This can be achieved by providing input lines with temperature sensors and heating or cooling jackets.

Following hydrogenation and any optional, although generally preferred low magnetic field treatment, the imaging agent is preferably mixed with water. The water used is preferably sterile and also preferably essentially free of paramagnetic contaminants. The resultant aqueous solution is then preferably treated to remove the hydrogenation catalyst, e.g. by passage through an ion exchange column, preferably one free of paramagnetic contaminants. The water may be temperature-controlled as may be a mixing chamber where water and imaging agent solutions are mixed so as to ensure the aqueous solution enters the ion exchange column at the appropriate temperature. Strongly acidic, sodium ion charged ion exchange resins such as DOWEX 1×2-400 (Dow Chemicals) and Amberlite IR-120 (both available from Aldrich Chemicals) resins may conveniently be used for the removal of typical metal complex hydrogenation catalysts. For fast ion exchange, the resin is preferably cross-linked to only a low degree, e.g. a 2% divinyl benzene cross-linked sulphonated, sodium ion loaded polystyrene resin.

Removal of the non-aqueous solvent may then conveniently be effected by spray flash distillation—e.g. by spraying the aqueous solution into a chamber, applying a vacuum, and driving the organic solvent free aqueous solution from the chamber using an inert, preferably non-paramagnetic gas, e.g. nitrogen. Indeed in general the flow of liquid components through the hydrogenation apparatus will preferably be effected using applied nitrogen pressure, e.g. 2 to 10 bar.

The resulting aqueous imaging agent solution may be frozen and stored or alternatively may be used directly in an MR imaging or spectroscopy procedure, optionally after dilution or addition of further solution components, e.g. pH modifiers, complexing agents, etc. Such direct use may for example involve continuous infusion or alternatively injection or infusion of one or more dose units. Bolus injection is particularly interesting.

The whole process from beginning of hydrogenation to end of solvent removal may conveniently be effected in less than 100 seconds, indeed it is feasible to produce dosage units in as little as 10 to 20 seconds, which is substantially less than $T_1$ for the imaging nuclei in many of the imaging agents in the contrast media so produced.

Desirably, the surfaces contacted by the imaging agent during the process of the invention are substantially free of paramagnetic materials, e.g. made of glasses as used for hyperpolarized $^3He$ containment as discussed in WO99/17304 or gold or a deuterated polymer. Surfaces contacting the non-aqueous solvent (e.g. acetone) should be acetone-resistant and valves may be magnetically controlled with solvent resistant Teflon or silicon parts.

The process of the invention may conveniently be automated and computer-controlled.

Viewed from a further aspect the invention provides a hydrogenation apparatus comprising a hydrogenation chamber having a liquid outlet into a conduit leading to a liquid droplet generator inlet (e.g. a spray nozzle) to a solvent removal chamber, said hydrogenation chamber having a hydrogen inlet and a solution inlet provided with a further liquid droplet generator, said conduit including a catalyst removal chamber (e.g. containing an ion exchange resin) between said hydrogenation chamber and said solvent removal chamber and being provided, preferably between said hydrogenation chamber and said catalyst removal chamber, with a liquid inlet (e.g. a water inlet), said solvent removal chamber being provided with a gas outlet (e.g. attached to a vacuum source) and with a liquid outlet (e.g. to an optional formulation chamber and thence to administration means or to a dose unit receiver (e.g. a syringe)), and said hydrogenation apparatus being further provided with magnetic shielding such that the magnetic field within at least part of said hydrogenation chamber and/or within at least part of said conduit (preferably the part upstream of the liquid (water) inlet) is <50 μT, more preferably <1 μT, most preferably <0.1 μT.

Clearly, if the process of the invention is performed directly in water using a water-soluble substrate and water-soluble catalyst, then the solvent removal chamber is not required.

The apparatus of the invention is preferably also provided with reservoirs and mixing chambers appropriate for the materials being fed in, e.g. an enriched hydrogen reservoir, a water reservoir, a reservoir for solutions of hydrogenation catalyst and/or hydrogenatable substrate, reservoirs for further contrast medium components, a mixing chamber for mixing solutions of catalyst and substrate, a mixing chamber for mixing water with the solution exiting the hydrogenation chamber, etc. Likewise the hydrogenation chamber is preferably provided with a vent for removing hydrogen and various of the chambers and reservoirs are preferably provided with nitrogen sources and nitrogen inlets to drive their contents into or through the apparatus. Particularly preferably, the apparatus also includes an enriched hydrogen generator, valves, valve actuators and a computer control for controlling apparatus operation.

The magnetic shielding is preferably removable so that it can be removed if $^2$H-imaging is desired.

The chambers and conduits of the apparatus of the invention are preferably sealable to prevent ingress of air; moreover, the apparatus is preferably provided with valves and ports arrangeable to permit degassing, in particular to remove surface adsorbed oxygen.

The water input to the apparatus of the invention is preferably deoxygenated, e.g. by treatment with nitrogen.

The "chambers" in the apparatus of the invention may have internal cross-sectional areas which are larger than the internal cross-sectional areas of the chamber inlets or outlets (in the flow direction); alternatively the cross-sectional areas in the flow direction may be substantially invariant, i.e. a tube may function as inlet-chamber-outlet.

The use of homogeneously catalysed "spray-hydrogenation" in the preparation of MR contrast agents is new. Likewise such hydrogenation is new in the preparation of amino acids and pharmaceuticals. The procedure is rapid and efficient and this forms a further aspect of the invention. Viewed from this aspect the invention provides a process for the preparation of an amino acid, a pharmaceutical or an in vivo diagnostic agent, characterised in that said process comprises a hydrogenation step in which a solution of a substrate and a hydrogenation catalyst is sprayed into a hydrogen-containing chamber.

Where the hydrogenation is effected using a gas in which the $^2$H:$^1$H ratio is in excess of 9:1, using p-D$_2$, the use of heterogenous catalysis is also contemplated—in this event catalyst removal may involve filtering or other particulate removal techniques.

The contents of all publications referred to herein are hereby incorporated by reference.

Referring to FIG. 1, hydrogen ($^1$H$_2$) from cylinder 1 is fed via tube 2 to a p-$^1$H$_2$ generator and thence into hydrogenation chamber 3. A hydrogenation catalyst solution from reservoir 4 and a hydrogenatable substrate solution from reservoir 5 are fed via lines 6 and 7 to a spray nozzle in chamber 3. The liquid settling in chamber 3 passes via conduit 8 through a twin μ-metal layered tube 9, a magnetic shield having an internal field of less than 0.1 μT, into an ion exchange column 10 and thence to a spray nozzle in the solvent removal chamber 11. Before the liquid enters the ion exchange column but after it exits the magnetic shielding, water from reservoir 12 is added via tube 13. Solvent removal chamber 11 is connected via tube 14 to a vacuum pump 15 which serves to remove non-aqueous solvent, e.g. acetone. The liquid remaining in chamber 11 is removed via exit duct 16.

Figure 2:
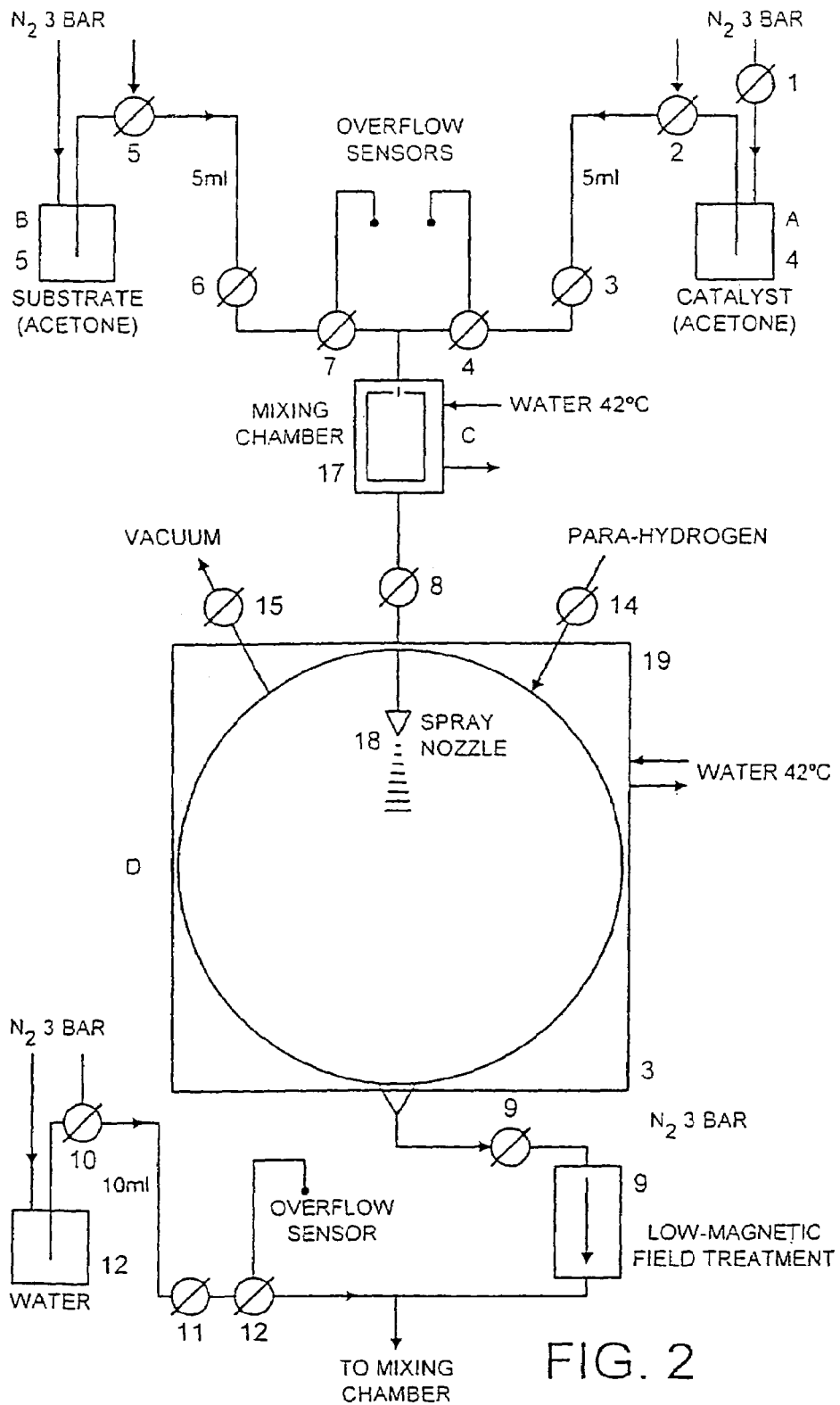
FIG. 2 is a schematic view of part of the apparatus of FIG. 1.
Figure 3:
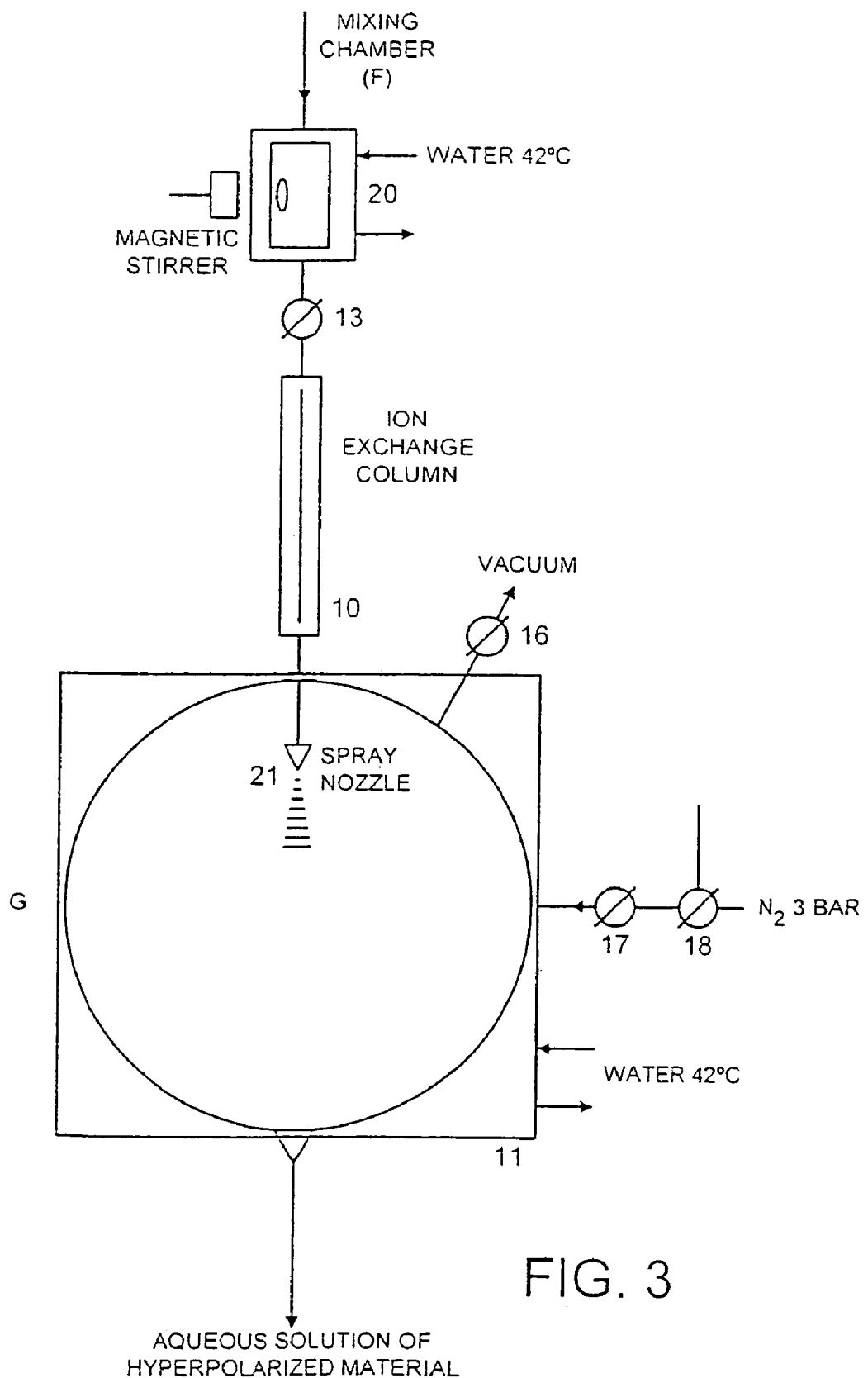
FIG. 3 is a schematic view of a further part of the apparatus of FIG. 1.

Referring to FIG. 2, it can be seen that nitrogen (at 3 bar) is used to drive catalyst and substrate solutions from reservoirs 4 and 5 to a water-jacketed mixing chamber 17 and thence to the spray nozzle 18 (which may be pneumatic) in hydrogenation chamber 3 which is provided with a valved hydrogen vent 19. Alternatively, the dosage and mixing of substrate and catalyst may be controlled by computer controlled pumps (not shown). Nitrogen may be used to drive the liquid collecting in the hydrogenation chamber through the magnetic shielding 9 to mix with nitrogen driven water from reservoir 12. Turning to FIG. 3, the solution/water mixture passes into water-jacketed mixing chamber 20 and thence through a 2 to 4 cm long ion exchange column 10 containing 400 mesh sulphonated polystyrene/2% DVB and on to spray nozzle 21 in solvent removal chamber 11. To ensure complete non-aqueous solvent removal, the chamber 11 is buffered with a cooling trap (not shown) followed by a second volume before the vacuum pump—this relieves the very sudden load otherwise put on the pump. After release from the chamber 11, the aqueous "contrast medium" is ready for use; alternatively its pH may be buffered and its ion profile adjusted (e.g. to add plasma cations).

There are two preferred modes of operation; in one the apparatus is used to fill a syringe which is removed and the contrast medium is injected; in the second, the apparatus delivers small doses of contrast medium continuously to a catheter linked to the patient. The second mode allows for easier imaging since the operator can adjust the MR imager to obtain a satisfactory image.

Figure 4:
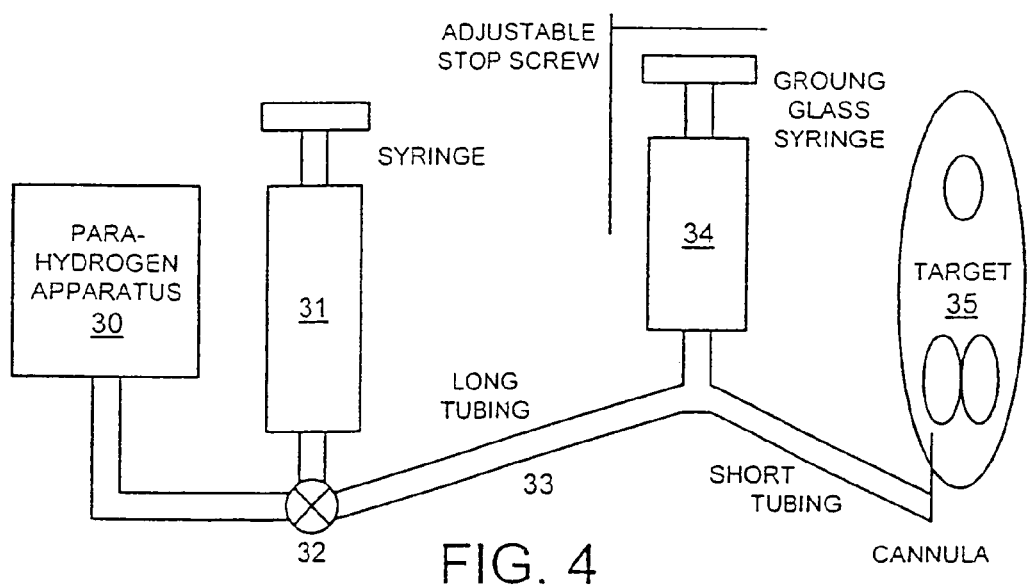
FIG. 4 is a schematic view of a further aspect of the present invention.

Referring to FIG. 4, the hyperpolarised solution is delivered by the apparatus 30 into a syringe 31. A 3-way switching valve 32 is connected. The syringe should be positioned vertically with the plunger-handle up to ensure the solution is free of air. By switching the valve 32 the solution can be injected to the transfer tube 33. A syringe or cavity 34 with determined volume and low friction is connected just before the injection target 35, and the syringe 34 absorbs the dead space and possible gas bubbles.

EXAMPLES 1

The following example is illustrative of certain preferred embodiments of the invention but is not intended to be illustrative of all embodiments.

A solution of (bicyclo[2.2.1]hepta-2,5-diene)-[1,4-bis (diphenylphosphino)butane]-rhodium(I) tetrafluoroborate (93.5 mg) in argon-bubbled acetone (5 ml) is charged in chamber A and a solution of 2-acetoxyacrylic acid (110 mg, 0.85 mmol) in argon-bubbled acetone (5 ml) in chamber B. Chamber E is filled with distilled, argon-bubbled water. Ion exchange resin of type sulphonated polystyrene, 2% cross-linked, swelled with water and charged with sodium ions is loaded in the ion-exchange column. Water at 42 C is circulated through the jackets in the set-up. The experiment is started by running a computer program that controls the valves according to scheme 1 as shown in Table 1 below. The program is written in LabView. After the program is finished the sample of aqueous hyperpolarized 0-acetyl lactic acid is removed at the bottom of chamber G by a syringe.

A 3 m$^3$/hr 2-stage diaphragm pump is used to provide the vacuum and 3 bar of nitrogen is used as the driving pressure.

The spray nozzles are ordinary commercial oil-burner nozzles, the one in chamber D is specified as 1.5 US gallon/hr with a 60 cone angle, the one in chamber G is 1.0 US gallon/hr with a 80 cone angle.

The magnetic valves are 8 W, 24V DC with gaskets of EPDM.

The magnetic screen is made from two concentric tubes of μ-metal.

TABLE 1

| Time/s | \multicolumn{18}{c}{Valve No.} | Comment |

| Time/s | 1 | 2 | 3 | 4 | 5 | 6 | 7 | 8 | 9 | 10 | 11 | 12 | 13 | 14 | 15 | 16 | 17 | 18 | Comment |
|---|---|---|---|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 | 0 | 0 | 0 | Start |
|  | 1 | 0 | 0 | 0 | 0 | 0 | 0 | 0 | 0 | 0 | 0 | 0 | 0 | 0 | 0 | 0 | 0 | 0 | Pressurise |
|  | 1 | 0 | 0 | 0 | 0 | 0 | 0 | 0 | 0 | 1 | 1 | 0 | 0 | 0 | 0 | 0 | 0 | 0 | Fill water loop until overflow is detected |
|  | 1 | 1 | 1 | 0 | 1 | 1 | 0 | 0 | 0 | 0 | 0 | 0 | 0 | 0 | 0 | 0 | 0 | 0 | Fill catalyst and substrate loops until overflow is detected |
| 0.2 | 0 | 0 | 0 | 1 | 0 | 1 | 1 | 0 | 0 | 0 | 0 | 0 | 0 | 0 | 0 | 0 | 0 | 0 | Add catalyst and substrate to C intermittently |
| 0.2 | 0 | 0 | 1 | 1 | 0 | 0 | 1 | 0 | 0 | 0 | 0 | 0 | 0 | 0 | 0 | 0 | 0 | 0 | Loop 15 times |
| 10 | 0 | 0 | 1 | 1 | 0 | 1 | 1 | 0 | 0 | 0 | 0 | 0 | 0 | 0 | 1 | 0 | 0 | 0 | Allow pressure to build up in C, evacuate D |
| 10 | 0 | 0 | 0 | 0 | 0 | 0 | 0 | 0 | 0 | 0 | 0 | 0 | 1 | 1 | 0 | 1 | 0 | 0 | Fill D with para-hydrogen, evacuate G |
| 12 | 0 | 0 | 1 | 0 | 0 | 1 | 0 | 1 | 0 | 0 | 0 | 0 | 1 | 0 | 0 | 1 | 0 | 0 | Spray mixture into D and dry overflow sensors |
| 5 | 0 | 0 | 0 | 0 | 0 | 0 | 0 | 1 | 1 | 0 | 0 | 0 | 0 | 0 | 0 | 1 | 0 | 0 | Suck reaction mixture to F |
| 8 | 0 | 0 | 0 | 0 | 0 | 0 | 0 | 0 | 0 | 0 | 1 | 1 | 0 | 0 | 0 | 1 | 0 | 0 | Add water and mix |
| 20 | 0 | 0 | 0 | 0 | 0 | 0 | 0 | 0 | 0 | 0 | 1 | 1 | 1 | 0 | 0 | 1 | 0 | 0 | Spray into G |
| 3 | 0 | 0 | 0 | 0 | 0 | 0 | 0 | 0 | 0 | 0 | 0 | 0 | 0 | 0 | 0 | 0 | 1 | 1 | Increase pressure in G |
| 3 | 0 | 0 | 0 | 0 | 0 | 0 | 0 | 0 | 0 | 0 | 0 | 0 | 0 | 0 | 0 | 0 | 1 | 0 | Equilibrate pressure in G with atmosphere |
|  | 0 | 0 | 0 | 0 | 0 | 0 | 0 | 0 | 0 | 0 | 0 | 0 | 0 | 0 | 0 | 0 | 0 | 0 | Finished |

EXAMPLE 2

The hyperpolarized solution is delivered by the para-hydrogen contrast agent apparatus to which a tube of length e.g. 50 mm is connected. A 3-way switching valve is connected to this tube, as a syringe. The syringe is placed vertically with the plunger pointing up to ensure the solution is free from air. The bubbles will float to the top and stay there. By switching the valve the solution can be injected into the transfer tube e.g. of length 3200 mm and a diameter of 0.76 mm. This gives a dead-volume of 1.5 ml. Just before the cannula "injection target" (e.g. a venflon or butterfly) a syringe with determined volume and low friction is connected with a 3-way tube. This syringe will collect the dead space and possible gas bubbles from transfer tubes. The plunger of the syringe is prevented from leaving the barrel by a stop-screw. When the syringe is full, the injected solution proceeds by the cannula to the target. Syringes with ground-glass barrel and plunger are suitable for this set-up.

With the equipment described above it was possible to inject 0.33 ml/s of physiological saline into the tail-vein of a rat.

It is apparent that many modifications and variations of the invention as hereinabove set forth may be made without departing from the spirit and scope thereof. The specific embodiments described are given by way of example only, and the invention is limited only by the terms of the appended claims.

The invention claimed is:

1. A hydrogenation apparatus comprising a hydrogenation chamber having a liquid outlet into a conduit leading to a liquid droplet generator inlet to a solvent removal chamber, said hydrogenation chamber having a hydrogen inlet and a solution inlet provided with a further liquid droplet generator, said conduit including a catalyst removal chamber between said hydrogenation chamber and said solvent removal chamber and being provided with a liquid inlet, said solvent removal chamber being provided with a gas outlet and with a liquid outlet.

2. An apparatus of claim 1, wherein said hydrogenation apparatus is further provided with magnetic shielding such that the magnetic field within at least part of said hydrogenation chamber and/or within at least part of said conduit is <50 µT.

3. An apparatus of claim 2, wherein said magnetic field is <1 µT.

4. An apparatus of claim 2 An, wherein said magnetic field is <0.1 µT.

5. An apparatus of claim 1, wherein said conduit is provided with a liquid inlet between said hydrogenation chamber and said catalyst removal chamber.

* * * * *